United States Patent [19]

Simon

[11] Patent Number: 5,031,634
[45] Date of Patent: Jul. 16, 1991

[54] ADJUSTABLE BIOPSY NEEDLE-GUIDE DEVICE

[75] Inventor: Morris Simon, Boston, Mass.

[73] Assignee: Beth Israel Hospital Assoc., Inc., Boston, Mass.

[21] Appl. No.: 467,690

[22] Filed: Jan. 19, 1990

[51] Int. Cl.$^5$ ............................................. A61B 10/00
[52] U.S. Cl. .................................................... 128/754
[58] Field of Search ............... 128/751, 752, 753, 754, 128/755; 606/211, 207, 46

[56] References Cited

U.S. PATENT DOCUMENTS

| | | | |
|---|---|---|---|
| 3,929,123 | 12/1975 | Jamshidi | 128/754 |
| 4,790,329 | 12/1988 | Simon | 128/754 |
| 4,799,495 | 11/1990 | Hawkins et al. | 128/754 |

Primary Examiner—Kyle L. Howell
Assistant Examiner—Robert L. Nasser, Jr.
Attorney, Agent, or Firm—David Prashker

[57] ABSTRACT

A unique adjustable biopsy needle-guide device is provided which allows it to be inserted accurately at a selected anatomic site; to be secured in an engaged position; to be disengaged on-demand into a moveable form; and to be repositioned at will. The guide device comprises a cannula with multiple wires and sliding member elements as a preassembled unit which can be sterilized and conveniently stored until required for use by the physician. The needle-guide serves as a guidepost for the surgeon to remove small or deep seated lesions or for precise placement of biopsy needles at the target site.

4 Claims, 6 Drawing Sheets

ADJUSTABLE BIOPSY NEEDLE-GUIDE DEVICE

RESEARCH SUPPORT

The research for the present inVention was supported by the Beth Israel Hospital Association.

FIELD OF THE INVENTION

The present invention is concerned with guiding instruments and devices used by physicians and surgeons to localize specific anatomic sites or diseased tissues in the body for biopsy or other purposes.

BACKGROUND OF THE INVENTION

Currently available radiologic imaging techniques make it possible to display a localized focus of disease deep within specific organs or tissues of the body. A typical example is the visualization of a small cancerous mass in the breast of a woman. In order to accurately diagnose and effectively treat the disease, it may be necessary for a surgeon to excise a portion of the diseased tissue for microscopic examination and analysis; or for a physician to accurately insert a needle into the mass to aspirate a sample of the abnormal cells or tissue fluid. A recurrent problem for the surgeon or physician is that even with the help of x-ray films, the search for a small lesion or mass often proves extremely difficult; can cause considerable damage to the normal tissues surrounding the lesion; and often fails in the attempt.

In recent years, increasingly sophisticated radiologic imaging methods with greatly improved resolution and tissue contrast have made it possible to identify small or deep-seated lesions in many anatomic sites. Frequently, however, the benign or malignant nature of the lesion remains uncertain. The diagnosis, clinical significance, and treatment may depend upon microscopic examination of tissue or cell samples obtained from the lesion by surgical biopsy if a large sample is required, or by needle biopsy if a small sample would suffice.

Originally, surgical exploration and biopsy were undertaken purely on the basis of the anatomic descriptions of the radiologic images, i.e., the organ or tissue involved and the described position of the lesion within the organ or tissue. Such surgical procedures were sometimes extremely difficult and prolonged because of the great mobility of soft tissues, limitations of surgical access, and imprecision of the descriptions. As a result, a variety of radiologic localization methods have evolved to facilitate and improve the accuracy of surgical and needle biopsy procedures:

a. Skin Markers: Initially, small radiopaque skin markers were placed directly over the target site under radiologic guidance. Indelible ink marks were then transferred onto the skin to guide the surgeon. This approach has proved satisfactory only for superficial lesions but is inadequate for deeper targets, particularly if these are affected by respiratory motion or posture.

b. Simple Needle Markers: Standard hypodermic needles or longer "spinal" needles have been used in the breast and other soft tissues, guided to the target site under radiologic imaging control. They are left in place for the surgeon. However, these marker needles are not well secured in the tissues and may move from their initial location during patient transfer to the operating room or when the patient position is changed.

c. Tissue-Staining Dyes: After placing a simple needle at the target site under radiologic control, various tissue-staining vital dyes have been injected into the soft tissues at the target site and sometimes also along the needle track. The intention is to direct the surgeon along the stained tract to the target tissue. However, the dyes frequently diffuse widely and have poor localizing value except in the hands of highly skilled operators.

d. Hookwires:

(i) The initial localizing wire hook for breast localization was described by Frank in 1979. The Frank localizer comprised a simple insertion needle containing a long thin wire with a hook end which projected through the needle point. The needle and wire are advanced into the tissues together; and the needle is withdrawn when close to the target lesion, leaving the flexible hookwire in place. The main disadvantage is the "one-way street" character of the method. The wire is designed only to be advanced; its position cannot be readjusted once it has been inserted. Furthermore, the wire is very flexible and can be inadvertently pulled out in a series of jerky step-like movements without great difficulty and may damage the tissues. In addition, the wire can be accidentally transected by the surgeon; and it can also incidentally work its way deeper into the breast tissues.

(ii) An improved hookwire was described by Kopans in 1981 with the hook portion initially housed within the needle lumen. With the Kopans device, the wire is released into the tissue only after the needle position is considered satisfactory. A thickened section of the wire was also provided proximal to the hook to reduce the chances of accidental transection. However, this hook is not readjustable once released; is not easily removable; can be accidentally severed; and unintentionally may advance deeper into the tissues. It can also be withdrawn accidentally in stepwise fashion.

e. Retractable Hookwires:

(i) A wire with a springy curved hook at its tip that can be withdrawn into its introducer needle is available and known as the Homer localizer. The Homer device allows repeated readjustment of the hook position so that accurate placement of the wire is possible. However, this also reduces the security of the wire which can be inadvertently withdrawn and displaced. The introducer needle can be removed or left in place depending on the radiologist's or surgeon's preference. There is a scythe-like action of the wire as it tries to regain its curved shape in the tissues and damage could occur.

(ii) An introducer needle with a side hole through which an anchored wire barb may protrude is now commercially available as the Hawkins localizer. Its structure is described within U.S. Pat. No. 4,799,495. The anchored hook of the device is retractable by advancing the internalized wire a short distance within the needle lumen, allowing the needle to be repositioned. This anchored hooked-needle design has considerable resistance to accidental withdrawal when the hook is extended. A slidable screw-stop is typically provided on the needle shaft to prevent deeper penetration of the needle and hook. In one variation, the hook can be advanced beyond the needle tip and the introducer needle removed. This leaves only a flexible wire in the tissues with the hook welded at its tip; a variation which is less secure. Other disadvantages include the rigidity of the needle; the risk of the hook advancing deeper unintentionally; and the possibility of breaking the junction between the wire and the hook.

(iii) A biopsy localization needle device with a single retractable side hookwire is described within U.S. Pat. No. 4,790,329. This device allows for on-demand repositioning; and permits the internal hookwire to be completely removed from the tissues and the localization device at will. Once in position, the hookwire extends into the tissues and avoids accidental withdrawal; the device, however, does not prevent an unintended, accidental advance deeper into the tissues.

Clearly, there remains a recognized and continuing need for an improved biopsy guide device which is held securely in the target tissue; is easily adjustable; is removable without destruction of localized tissue; eliminates the need for additional guide devices; and provides a reliable guidepost for the surgeon or physician to follow. The availability of such an improved biopsy guide would be recognized and acknowledged by physicians and surgeons alike as being a valuable advance in this art.

SUMMARY OF THE INVENTION

The present invention is an improved, adjustable biopsy guide device comprised of:

a cannula comprising a substantially tubular wall, an internal lumen, an open end, and having at least one aperture in the tubular wall towards the open end of the cannula, and at least one slot in the tubular wall towards the other end of the cannula, the slot being in substantial alignment with the aperture;

a first sliding member disposed adjacent to a portion of a slot in the tubular wall;

a second sliding member disposed adjacent to another portion of a slot in the tubular wall;

a first wire rod within the lumen of the cannula, this first wire rod having a barb-like end extendable and retractable through the aperture in the tubular wall, and a fixed end fixed to the first sliding member, the barb-like end of this first wire rod being extendable and retractable on-demand by moving the first sliding member;

a second wire rod within the lumen of the cannula, this second wire rod having a pointed tip extendable and retractable through the open end of the cannula, a barb-like appendage extendable and retractable through the aperture in the tubular wall, and a fixed end fixed to the second sliding member, the pointed tip and the barb-like appendage being extendable and retractable on-demand by moving the second sliding member; and means for reciprocally moving the first and second sliding members in opposing directions on-demand.

BRIEF DESCRIPTION OF THE DRAWING

The present invention may be more easily and completely understood when taken in junction with the accompanying drawing, in which.

DETAILED DESCRIPTION OF THE INVENTION

Figure 1:
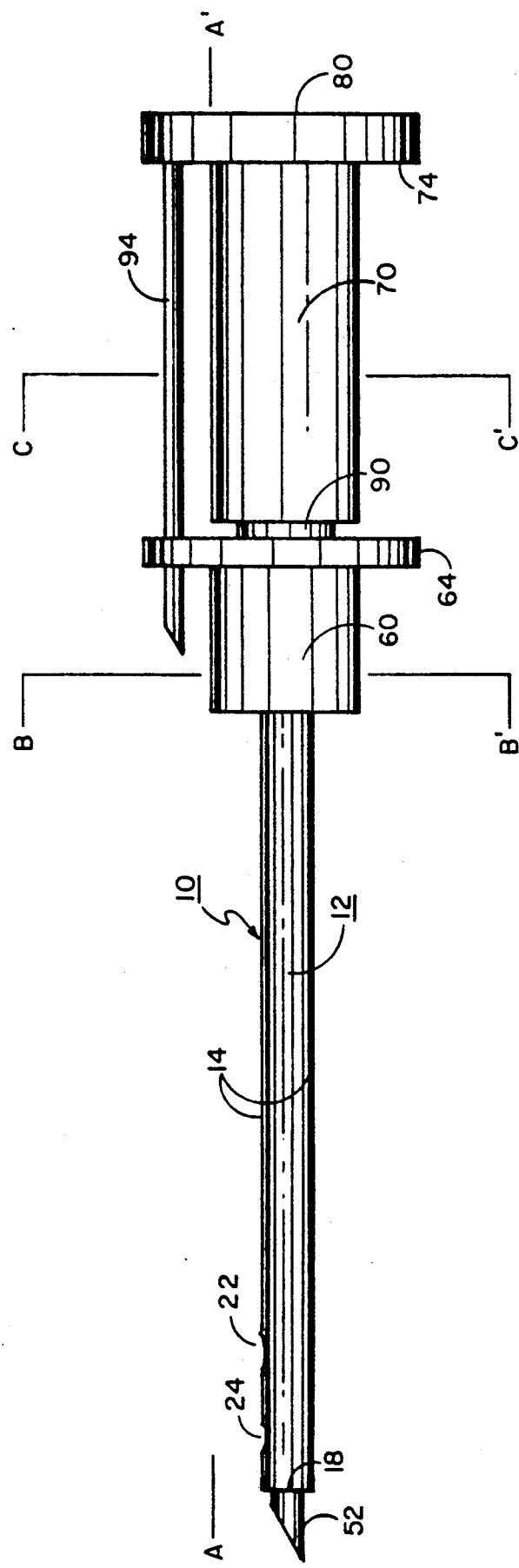
FIG. 1 is a side view of a preferred embodiment comprising the present invention in a retracted state.

The improved biopsy guide is a needle-like device which can be inserted into the breast, liver, muscle, or other soft tissues, with the aid of radiologic imaging, to firmly grip and localize a small or deep-seated lesion for accurate biopsy, aspiration or excision. The guide has two operational forms: initially, with the barbs retracted and the pointed tip extended, it is a long thin, smooth, sharp-pointed needle device whose shaft can be easily advanced through the tissues to the target lesion. Subsequently, when the guide has reached an intended position within the tissue, the needle point can be retracted and two converging barbs extended from the interior of the shaft to grip the target tissue with a staple-like action that locks the guide in place securely. The guide is readily readjustable, if necessary; and can thus be repositioned on-demand with great precision. It then remains locked in place to serve as a secure, accurate and reliable guidepost for the operator. The guide handle can also optionally be used to support, accurately aim, and direct an aspiration biopsy needle or tissue cutting needle to the target lesion in order to obtain small cytologic or histologic samples without surgery.

The improved guide device provides a number of advantages to the user:

a. Ease of Handling: A simple thumb press action using one hand converts the guide device from its locked, barb-extended form to its movable point-extended form, or vice versa. Either form can be maintained as long as necessary with a built-in latch. The one-action movement simultaneously and reciprocally moves each of the two barbs in opposite directions and also retracts or advances the needle point.

b. Security: The tissue-gripping staple-like arced action of the opposing extendable barbs and the blunt shaft tip secure the end of the guide device in the tissues with little risk of displacement in either direction. The guide will not dislodge en route to the operating room or during the surgical dissection. The skin of the patient can be allowed to slide along the shaft freely since the tip remains fixed at the target site; and there is no need for an uncomfortable skin-stop clamp during transportation.

c. Readjustability: The simple switching between locked and movable forms of the device permits precise placement of the guide tip within or adjacent to the target lesion. The preferably small gauge of the guide device shaft and its sharp needle point allow easy penetration of the soft tissues.

d. Non-Transectability: The preferred 23 gauge needle shaft lumen is almost filled by the preferred two half round stainless steel wire rods and resists accidental transecion during surgery.

e. Surgical Convenience: The easily palpable shaft and security of the guide tip allow the surgeon to dissect the target lesion without fear of dislodging or transecting the device during surgical manipulation.

f. Aiming and Depth—Control of Biopsy Needles: The guide device can be used to direct a variety of separate aspiration biopsy needles or tissue cutting biopsy needles to the target lesion with great confidence. Sets of aligned holes are provided in the handle to aim and also to control the depth of these needles, different hole sizes serving various needle gauges. This ensures optimum sample quality for microscopy and enhances the value of a "negative for malignancy" result. Biopsy sampling can be repeated as often as necessary without displacing the guide. Since the tissue-securing function of the guide is separated from the biopsy-taking function of the biopsy needles, the guide offers a major advantage that other localization and biopsy systems lack.

g. Preassembly: The guide device is intended to be supplied ready for use, fully preassembled and presterilized. It requires no handling of the wire inserts by the user.

It will be noted and appreciated also that a diverse variety of uses and applications are envisioned for the present invention. A representative descriptive range of applications and uses is provided hereinafter.

1. Imaging Methods: Precise placement of the guide device comprising the present invention at the target tissue site may be controlled by a variety of radiologic imaging methods. Mammography, standard radiography, fluoroscopy, computerized tomography, or ultrasound may be used to visualize the target lesion. These enable the best skin entry point to be selected; the required direction and depth of the shaft to be determined; and may also be used to monitor its passage through the tissues. The guide device is inserted manually in most instances but stereotactic needle guiding apparatus may also be employed to support and direct the guide with great precision.

Since the guide device will likely contain ferromagnetic stainless steel components, it is not deemed suitable for use with magnetic resonance imaging; however, nonmagnetic materials could be used in the making of the guide device if necessary or desired under such circumstances.

2. Mammographic Localization: The adjustable guide device is particularly well suited to localization of small non-palpable lesions in the breast by mammography. Typically, just prior to the scheduled surgical biopsy procedure, the breast is compressed in the mammography unit using a special compression plate with a rectangular biopsy window positioned over the suspected region. A film is obtained and the exact location of the lesion is determined using the radiopaque coordinates provided along the edges of the window. After cleansing the skin over the lesion, the guide device is inserted into the breast parallel to the chest wall at the x-y coordinates of the particular lesion. Since the needle tip of the shaft is very thin, local anesthetic is generally unnecessary. The guide device will usually be advanced beyond the expected target depth so that the lesion is actually penetrated by the device. The multiple barbs of the guide are then extended to lock the device in place. The depth of the guide is indicated by the centimeter markings provided on the shaft.

A second film is normally taken to document an end-on view of the device to confirm its correct relationship to the lesion. If this is unacceptable, the barbs are retracted; the needle shaft partly withdrawn; and its position readjusted. Once the needle shaft is properly positioned, the initial breast compression is released and the compression reapplied in a plane parallel to the guide-shaft. Another film is taken to demonstrate the longitudinal relationship between the needle tip and the lesion viewed from the side. If necessary, an adjustment of the depth of the guide device can be made so that the target tissue is securely transfixed at the tip of the needle guide.

An alternative approach, preferred by some surgeons, is to insert the guide device into an uncompressed breast at the intended incision site, and then advance it toward the target site. In this case, the direction and depth are judged by analysis and measurement of the prior mammography films with due allowance being made for the tissue compression. The depth of the tip is preferably indicated by centimeter calibration markings on the needle shaft. The guide device is secured in this estimated position by the extended barbs. The breast is now compressed in a plane parallel to the needle shaft, and a mammogram film is obtained. The breast is then typically compressed in a second plane at right angles to the first plane, but still parallel to the needle shaft; and another mammogram film is obtained. The two films thus define the relationship between the end of the needle and the lesion. If this spatial relationship is found to be unsatisfactory, the position of the guide can be adjusted appropriately; and the taking of compression films repeated until the needle tip is shown to be accurately located at the desired target site. The risk of accidental penetration of the anterior chest wall with a frontal approach is minimized by the secure fixation provided by the twin barbs and blunt needle tip. This allows the surgeon to dissect along the needle shaft to reach the biopsy target, a simpler and more direct method which also allows excision of the track of the guide needle to minimize the risk of seeding malignant cells.

Once the needle tip of the guide is correctly positioned, the skin entry area is typically covered with sterile gauze and the handle of the guide may also be covered by small paper cup taped over it. Alternatively, the handle may be loosely taped directly to the patient's chest. The skin of the breast is able to slide freely along the shaft of the guide; thus even if the patient moves her arms or changes posture, the lesion itself remains firmly secured at the end of the needle shaft in the depths of the breast. It is not necessary to use any skin-stop attachment on the guide shaft to prevent skin sliding or accidental deeper penetration of the tissues. The patient is transferred to the operating room with the guide device in place for the surgical biopsy.

3. Surgical Breast Biopsy: The surgeon normally previews and discusses the localization films with the radiologist to plan an optimum access route to the lesion so as to minimize tissue trauma and scarring. The dissection can proceed according to the surgeon's preferred technique. The lesion is well secured at the end of the guide's shaft and cannot be easily dislodged. The cannula lumen of the device is almost completely filled by two strong stainless steel wire rods and will resist accidental cutting during the dissection procedure, a problem that has been encountered with previous localizing hookwires.

If the dissection follows the direction of the guide shaft, the distance remaining to the lesion at any point during the operation is indicated by the shaft calibrations markings. The biopsy specimen can be removed with the guide device still fixed in place within it. The specimen may be x-rayed, if so desired, and then sent to the pathologist for microscopy. The film of the tissue specimen and guide may help the pathologist find a small target lesion within the specimen.

If the dissection is performed by approaching the tissue target at the tip of the shaft from the side, the surgeon is then guided by the orientation of the guide's handle; by the centimeter calibrations on the shaft; and by palpation of the shaft through the tissues. The shaft is easily palpable during dissection if it is jiggled slightly. Once the biopsy sample or lesion has been dissected free, the guide device can be released and withdrawn along its own track so that the tissue sample may be removed separately along the dissection path. The specimen is x-rayed and/or sent to Pathology for processing in the usual way.

4. Surgery of Other Sites: In addition to breast biopsy localization, the guide device may be used to assist the biopsy or removal of small lesions from a variety of other anatomic sites. It can direct the surgeon to a small or deep-seated lesion in the liver, lung, kidney, or brain, though these new applications must await further investigation to assess their clinical value and risks. The guide device can also prove helpful in removing foreign bodies such as a needle fragment or radiopaque glass shard from the tissues of the hand or foot, or a bullet from the buttock or chest wall. The device may also serve to mark the vertebral level required for a laminectomy or fusion procedure of the spine.

The operator will select the most suitable imaging modality depending upon the inherent contrast of the lesion or foreign body, its anatomic location, the availability and cost of various imaging procedures, and the collaborating radiologist's experience and preference. The guide device is readily usable with standard radiography, fluoroscopy, computerized tomography, or ultrasound. The images obtained must be pluridirectional or cross-sectional so that 3-dimensional coordinates can be determined; an entry point selected; and the target depth measured. This permits the guide to be accurately aimed, inserted, advanced through the tissues to the required depth, and locked into place at the target site. The required angle of insertion may be guided by a goniometer or protractor held by an assistant; or else the guide can be supported by an adjustable stereotactic device attached to the patient's skin, or, less satisfactorily, to the table top.

If fluoroscopy is the selected imaging modality, a plastic side-arm attachment can be used to hold the handle of the device while it is being aimed or advanced into the tissues. This avoids exposing the operator's hands to the primary x-ray beam. The needle-guide may also be useful to a surgeon without radiologic imaging as a non-crushing alternative to a forceps to grasp a deeply located tissue under direct vision.

DETAILED DESCRIPTION OF A PREFERRED EMBODIMENT

Figure 2:
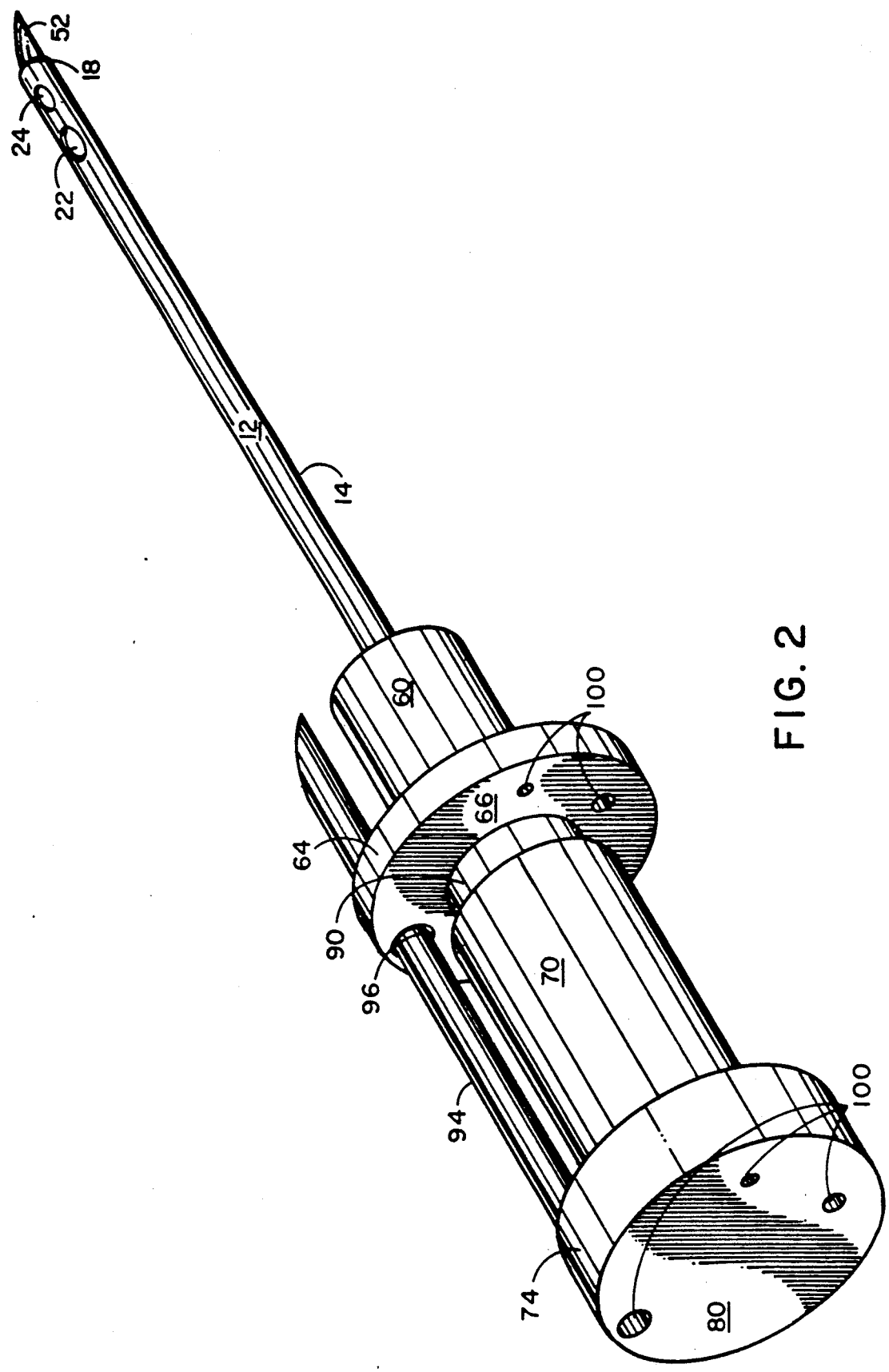
FIG. 2 is a perspective view of the preferred embodiment illustrated by FIG. 1.
Figure 3:
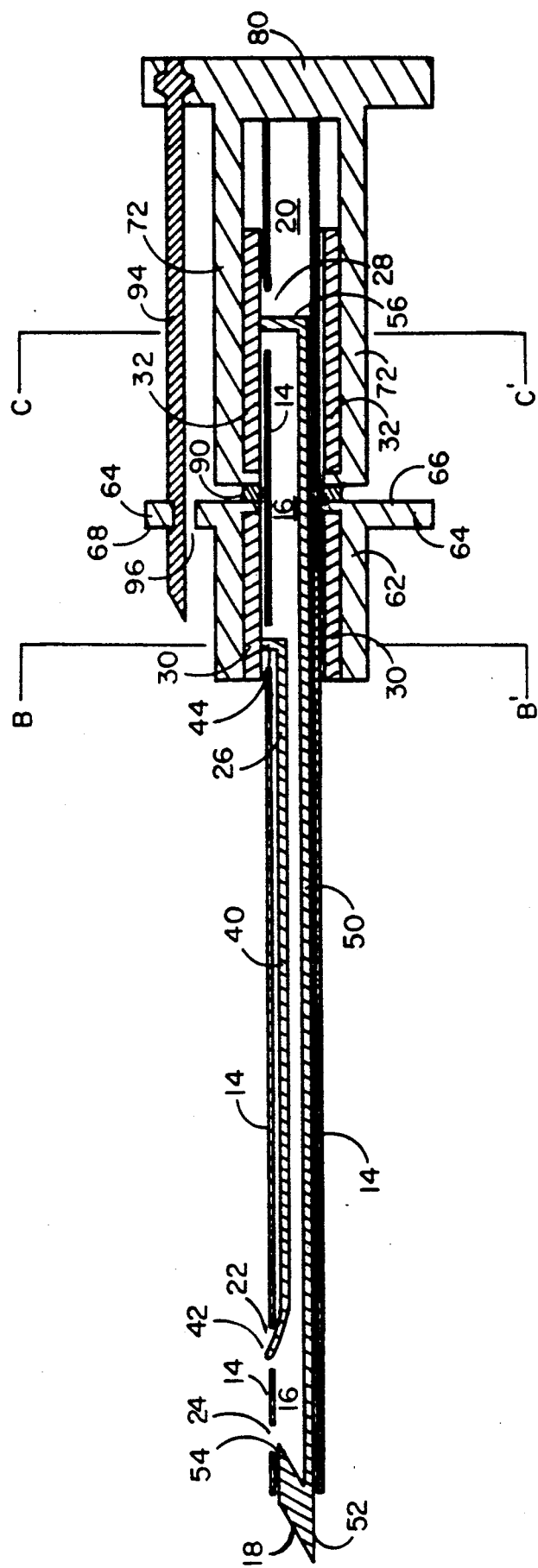
FIG. 3 is a cross-sectional view of the preferred embodiment illustrated by FIG. 1 along the axis AA'.
Figure 5:
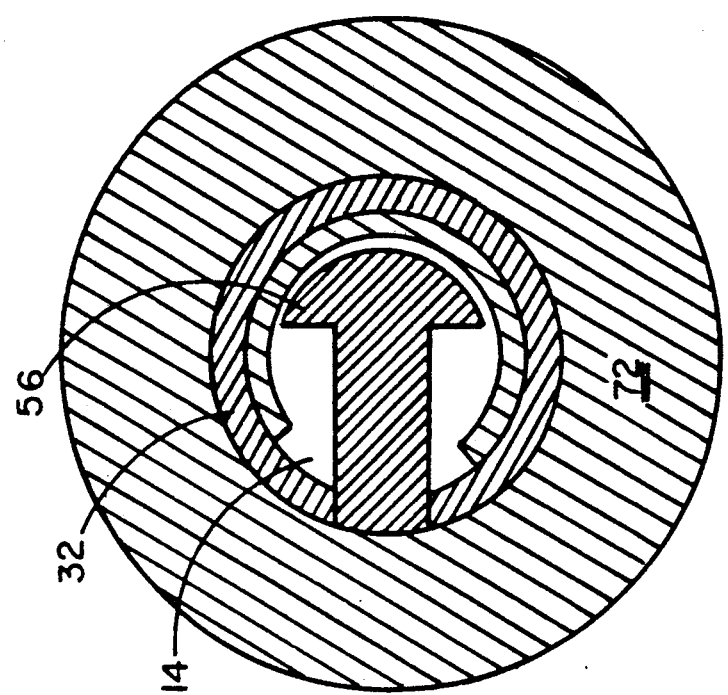
FIG. 5 is a cross-sectional view of the preferred embodiment illustrated by FIG. 1 along the axis CC'.
Figure 6:
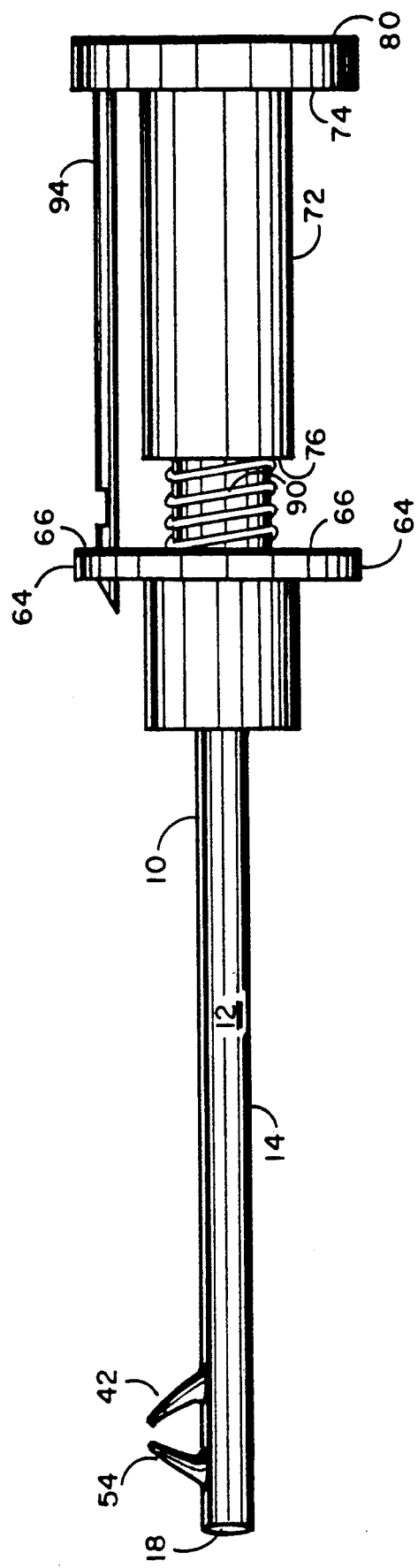
FIG. 6 is a side view of the preferred embodiment illustrated by FIG. 1 when in a barb-extended state.
Figure 7:
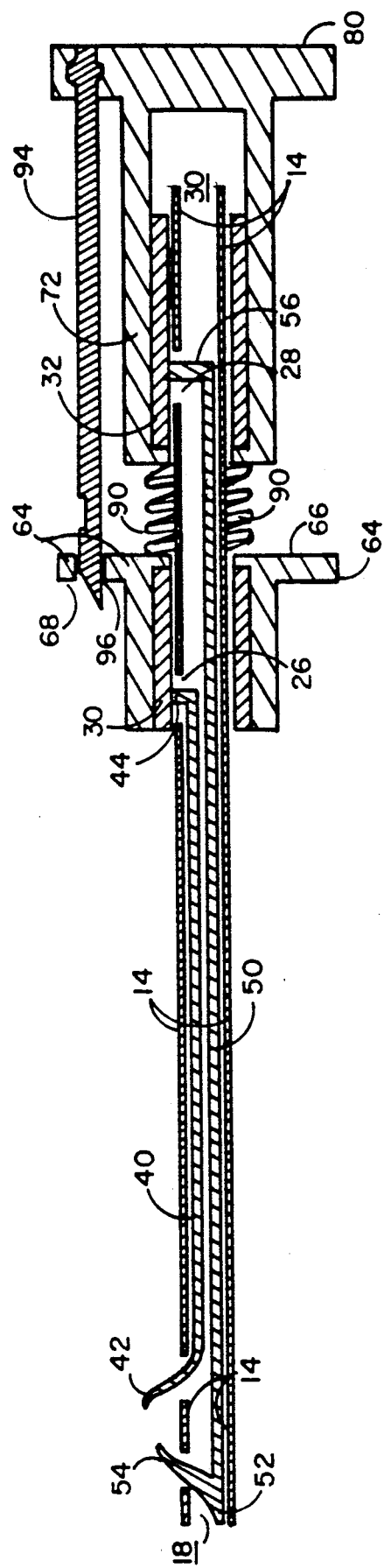
FIG. 7 is a cross-sectional view of the barb-extended embodiment illustrated by FIG. 6.

Detailed illustrations of a preferred embodiment comprising the guide device of the present invention are provided by FIGS. 1–7 respectively. FIGS. 1 and 3 provide detailed views of the preferred guide device in the barb-retracted format to be employed when inserting the guide device into the tissues of a subject. In comparison, FIGS. 6 and 7 illustrate the barb-extended format for the guide device which locks, holds, and retains the inserted guide device at a single desired position or location within the tissue mass. Direct comparison of FIGS. 1 and 3 with FIGS. 6 and 7 will aid in understanding the essential and critical components of the present invention.

Alternate views of the adjustable guide device in its barb-retracted form are provided by FIGS. 1–3 respectively. As seen therein, the guide device 10 is comprised of an elongated cannula 12 comprising a substantially cylindrical tubular wall 14, an internal lumen 16, an open end 18, and a covered end 20. Towards the open end 18 there is at least one aperture; in this preferred embodiment, there appear a first aperture 22 and a second aperture 24 in the tubular wall 14. Towards the covered end 20 of the cannula 12, there is at least one open slot; in this preferred embodiment, there appear a first slot 26 and a second slot 28 in the tubular wall 14.

Disposed upon the exterior surface of the cannula 12 adjacent to at least a portion of a slot in the tubular wall 14 are a first sliding member 30 and a second sliding member 32. Within the illustrated preferred embodiment, the first sliding member 30 is disposed adjacent to the first slot 26; correspondingly, the second sliding member 32 is disposed adjacent to the second slot 28 in the tubular wall 14.

Figure 4:
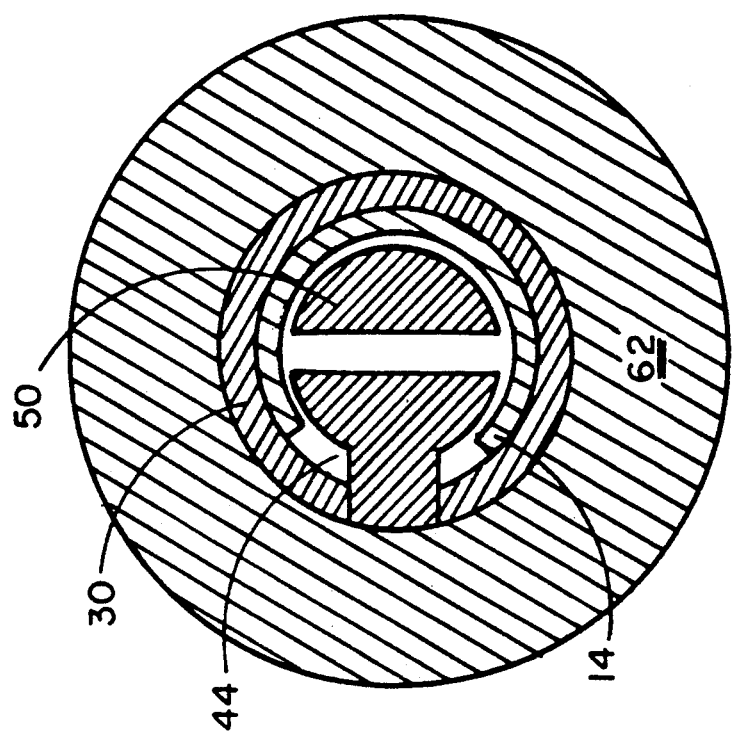
FIG. 4 is a cross-sectional view of the preferred embodiment illustrated by FIG. 1 along the axis BB'.

As illustrated by FIGS. 4 and 5 respectively, in the preferred embodiments the first sliding member 30 and the second sliding member 32 are configured as hollow cylinders disposed upon the exterior surface of the cannula 12; and which are able to slide along the exterior surface of the tubular wall 14 in directions parallel to the central axis of the cannula 12. While the preferred embodiment of the first sliding member 30 and the second sliding member 32 is seen as a completely encircling cylinder, there is no essential requirement or demand that a complete encirclement of the tubular wall 14 be made by either the first or the second sliding members. Moreover, it is neither essential nor required that the first sliding member 30 or the second sliding member 32 actually be disposed on the exterior surface of the tubular wall 14. To the contrary, it is only required that the sliding member itself exist in a definable configuration and dimensions; and be disposed adjacent to at least a portion of a slot formed within the tubular wall of a cannula. Accordingly, neither the configuration, nor dimensions, nor materials, nor nature of disposition or manner of affixation, nor the manner or mechanism of sliding capability are of any importance or particular relevance to the subject matter of the present invention.

Within the lumen of the cannula 12 are at least two different movable wire rods which within the preferred embodiments are formed as metallic, half-rounded wire rods having substantial tensile strength and resiliency. The first half-round wire rod 40 has a barb-like end 42 and a fixed end 44 joined and fixed permanently to the first sliding member 30. The barb-like end 42 is extendable and retractable through an aperture 22 in the tubular wall 14 as the first wire rods 40 moves within the lumen 16. In comparison, the second half-rounded wire rod 50 has a pointed tip 52, a barb-like appendage 54, and a fixed end 56 joined and permanently fixed to the second sliding member 32. The barb-like end 54 is intended to be extendable from and retractable through an aperture 24 in the tubular wall 14 as the second wire rod 50 moves within the lumen 16. Simultaneous with the movement of the barb-like appendage 54 through the aperture 24, the pointed tip 52 will be extended from and withdrawn through the open end 18 of the cannula 12. Note however that the directional movement of the pointed tip 52 is opposite to the movement of the barb-like appendage 54. As the tip is extended, the barb-like appendage recedes; conversely, as the pointed tip is retracted, the barb-like appendage becomes extended through the aperture.

It will be also recognized and appreciated that the first wire rod 40 and the second wire rod 50 are intended to move within the lumen 14 in reciprocal, but completely opposing directions concurrently or simultaneously during the process of either extension or retraction of the barb-like end 42 and the barb-like appendage 54 through their respective apertures. This is best illustrated by comparing the positioning and alignment of the first sliding member 30 and the first wire rod 40 with the positioning and alignment of the second sliding member 32 and the second wire rod 50 - both in the retracted state illustrated by FIGS. 1 and 3 in the extended state illustrated by FIGS. 6 and 7 respectively. It will be noted that when in the barb-retracted format for the device, the barb-like end 42 of the first wire rod 40 and the barb-like appendage 54 of the second wire rod 50 remain withdrawn and lie within the lumen 16 of the cannula 12; and that the positioning of the first sliding member 30 is proximal or very close to the positioning of the second sliding member 32 as each of these are disposed on the exterior surface of the tubular wall 14. In this state, the pointed tip 52 of the second wire rod 50 extends through the open end 18 and serves as the cutting tip or edge for the guide device 10 as a whole.

In comparison, when the sliding members 30 and 32 respectively are moved apart reciprocally in opposing directions, the changes illustrated within FIGS. 6 and 7 respectively occur concurrently or simultaneously: the barb-like end 42 of the first wire rod 40 is moved forward (in the direction towards the open end 18) and becomes extended through the aperture 22 to its maximum degree. Simultaneously, the barb-like appendage 54 and the pointed tip 52 of the second wire 50 are moved backward (in the direction towards the covered end 20 of the cannula 12); by this opposite directional movement for the second wire rod 50, the barb-like appendage 52 becomes extended through the second aperture 24 and the pointed tip 52 is withdrawn through the open end 18 to lie within the internal lumen 16 of the cannula 12. Accordingly, it is seen that by this reciprocal, but directionally opposite movement for the sliding member 30 in comparison to the direction of the second sliding member 32, each wire rod 40 and 50 has been reciprocally moved in opposing directions within the lumen of the cannula. Nevertheless, although the wire rods individually have reciprocally moved apart in opposite directions, both the barb-like end 42 of the first wire rod 40 and the barb-like appendage 54 of the second wire rod 50 become extended through their respective apertures; and move towards each other from opposing directions in a common plane of alignment. It will be recognized and appreciated therefore that any means for reciprocally moving the first sliding member 30 and second sliding member in opposing directions will cause the concurrent or simultaneous extension of the barb-like appendage 54 and the barb-like end 42. Conversely, should each sliding member be reciprocally moved in a reverse, but mutually opposing direction, the previously extended barb-like appendage 54 and the barb-like end 52 will become mutually retracted and withdrawn back into the lumen 16 of the cannula 12. The pointed tip 52 of the second wire rod 50 will also act in unison to extend and be withdrawn concurrent with the reciprocal movement of the first and second sliding members.

A preferred means for reciprocally moving the first sliding member 30 and the second sliding member 32 and their correspondingly affixed wires 40 and 50 is illustrated within FIGS. 1, 3, 6, and 7 cumulatively. As shown within the preferred embodiment therein, a spring-loaded, single action apparatus for reciprocally moving the first sliding member 30 and the second sliding member 32 is provided which comprises: a first substantially cylindrical mounting 60, a second substantially cylindrical mounting 70 with an expanded plunger head 80, a coiled spring 90, and a movable latch 94. It will be recognized and appreciated that the first cylindrical mounting 60 and the second cylindrical mounting 70 are substantially similar both in structure and appearance within this embodiment. The first cylindrical mounting 60 itself comprises a column body 62 and a raised flange 64 which provides a ledge surface 66. As noted within FIGS. 4 and 5 respectively, it is noted that the entirety of the first cylindrical mounting 60 is attached to and preferably supported by the first sliding member 30. The cylindrical mounting 60 is intended to act as the structure for physically moving the first sliding member 30 forwards towards the open end 18 or rearward towards the covered end 20 reciprocally; but always opposite to the movement of the second sliding member 32 regardless of exact direction. Thus, the first sliding mounting 60 is joined directly to only the first sliding member 30 alone and is not attached to the cannula 12. A second cylindrical mounting 70 is mounted upon and attached to the second sliding member 32. The second substantially cylindrical mounting 70 is comprised of a column body 72, a raised flange 74 which provides a ledged surface 76. The manner of juncture and mounting for the second cylindrical mounting 70 to the second sliding member 32 is preferably identical to that described for the first sliding member 30 and the first cylindrical mounting 60 described previously.

A plunger head 80 forms part of to the column body 72 of the second cylindrical mounting 70. The plunger head 80 as shown encompasses and envelopes, but is not directly attached to the covered end 20 of the cannula 12. Rather as illustrated within FIG. 3 and FIG. 7, the plunger head moves relative to the covered end 20 together with the sliding member 32. Joined to and separating the ledge surfaces 66 and 76 is a coiled spring 90. When the guide device is in the retracted state illustrated within FIG. 3, the coiled spring 90 is compressed; and being compressed is able to exert an expansion (or tension) force upon each of the ledge surfaces 66 and 76. When released, this force will move the cylindrical mountings 60 and 70 spatially apart in mutually opposing directions simultaneously. To maintain the expansion force provided by the compressed coiled spring 90 and to prevent movement of the sliding members and their corresponding wires, a holding latch 94 is pivotably joined to the plunger head 80. This latch 94 is able to pivot radially and has been dimension ⓡd such that the latch can engage and hold the underside 68 of the flange 64 comprising part of the first cylindrical mounting 60. The flange 64 is preferably provided with a rectangular opening 96 to engage the latch 94 conveniently; and to provide for quick and easy release of the latch with the subsequent initiation of reciprocal spring-driven movement in opposite directions by the first and second sliding members individually. A perspective view of the latch 94 from its pivotable rotable junction on the plunger head 80 and in position at the underside 68 of the first cylindrical mounting 60 is provided by FIG. 2.

The effect of disengaging the latch 94 from the underside 68 of the first cylindrical mounting 60 causes a conversion of the guide 10 from the barb-retracted state illustrated within FIGS. 1 and 3 into the barb-extended format of FIGS. 6 and 7. As seen within FIGS. 6 and 7, the coiled spring 90 has released its force upon the cylindrical mountings 60 and 70; and consequently caused the sliding members 30 and 32 respectively to move reciprocally in opposite directions. The result of releasing the extension force provided by the coiled spring 90 is an extension through their respective apertures of the barb-like end 42 and barb-like appendage 54 and a retraction and withdrawal of the pointed tip 52 to a position well inside the internal lumen 16 of the cannula 12. This is the locked or barb-extended state for the guide device after it has been determined that the guide device has been physically positioned in the tissues of the subject at the appropriate and desired location. Once in the barb-extended, locked position, the guide device will remain motionless and held in position by the extended barb-like appendage 54 and the barb-like end 42 indefinitely.

Should it become necessary or desirable to move or reposition the guide device itself, the user by a single action movement of his fingers can exert a compression force upon the cylindrical mountings 60 and 70. In exerting such a compression force upon the cylindrical mountings, the user will cause a reciprocal movement towards each other from opposing directions between the first sliding member 30 and the second sliding member 32 with the consequential compression of the coiled spring 90. The latch 94 is then automatically repositioned and locked via the opening 96 of the raised flange 64 allowing the needle guide 10 to hold and maintain the compressed positioning of the first and second sliding members. The overall result of exerting such a compression force is to cause a conversion of the guide device from the barb-extended state back into the barb-retracted state illustrated by FIGS. 1 and 3 respectively. The movement of the sliding members 30, 32 reciprocally but in opposite directions towards each other will cause the barb-like appendage 54 and the barb-like end 42 to recede and become retracted back into the internal lumen 16 of the cannula 12. Simultaneously, the pointed tip 52 will become extended again and advance through the open end 18 to a leading position beyond the blunt cannula 12.

An optional but desirable feature of the guide 10 is illustrated by FIG. 2. A series of paired portals or holes 100 of various sizes has been made through the flange 64 of the first cylindrical mounting 60 and the head 80 of the second cylindrical mounting 70. Each matched pair of portals 100 is aligned on an axis converging slightly toward the central axis of the cannula 12. These aligned portals provide an aligned pathway for the introduction of fine bore aspiration needles, tissue-cutting biopsy needles, tissue-cutting loops or knives, and other long instruments which may be used to advantage during a surgical procedure. The portals are aimed and aligned, preferably, at the open end 18 of the guide device. These portals 100 thus provide a precise pathway for aligned positioning of other instruments to increase the accuracy of their placement within the target tissue and to minimize the incidental surgery and damage to the tissues and discomfort for the patient.

The invention is not to be restricted in form nor limited in scope except by the claims appended hereto.

What I claim is:

1. An adjustable biopsy guide device comprised of:
    a cannula comprising a substantially tubular wall, an internal lumen, an open end, at least one aperture in said tubular wall towards said open end of said cannula, and at least one slot in said tubular wall towards the other end of said cannula, said slot being in substantial alignment with said aperture;
    a first sliding member disposed adjacent to at least a portion of said slot in said tubular wall;
    a second sliding member disposed adjacent to at least another portion of said slot in said tubular wall;
    a first rod within said lumen of said cannula, said first rod having a barb-like end extendable and retractable through said aperture in said tubular wall and a fixed end fixed to said first sliding member;
    a second rod within said lumen of said cannula, said second rod having a pointed tip extendable and retractable through said open end of said cannula, a barb-like appendage extendable and retractable through said aperture in said tubular wall, and a fixed end fixed to said second sliding member; and
    at least one compressible spring fixed to said first and seconding sliding members for reciprocally moving said first and second sliding members in opposing directions on-demand.

2. An adjustable biopsy guide device comprised of:
    a cannula comprising a substantially tubular wall, an internal lumen, an open end, first and second apertures in said tubular wall towards said open end of said cannula, and first and second slots in said tubular wall towards the other end of said cannula, said slots being in substantial alignment with said apertures;
    a first sliding member disposed adjacent to said first slot in said tubular wall;
    a second sliding member disposed adjacent to said second slot in said tubular wall;
    a first rod within said lumen of said cannula, said first rod having a barb-like end extendable and retractable through said first aperture in said tubular wall and a fixed end passing through said first slot in said tubular wall and being fixed to said first sliding member;
    a second rod within said lumen of said cannula, said second rod having a pointed tip extendable and retractable through said open end of said cannula, a barb-like appendage extendable and retractable through said second aperture in said tubular wall, and a fixed end passing through said second slot in said tubular wall and being fixed to said second sliding member; and
    at least one compressible spring fixed to said first and seconding sliding members for reciprocally moving said first and second sliding members in opposing directions on-demand.

3. The adjustable guide device as recited in claim 1 or 2 wherein each said rod is half-rounded along its length.

4. The adjustable biopsy guide device as recited in claim 1 or 2 further comprising means for maintaining said spring-fixed first and second sliding members under reciprocally opposing forces.

* * * * *